(12) United States Patent
Nataneli et al.

(10) Patent No.: US 10,424,225 B2
(45) Date of Patent: Sep. 24, 2019

(54) METHOD FOR ULTRASOUND TRAINING WITH A PRESSURE SENSING ARRAY

(71) Applicant: SonoSim, Inc., Santa Monica, CA (US)

(72) Inventors: Gabriele Nataneli, Beverly Hills, CA (US); Eric Savitsky, Santa Monica, CA (US)

(73) Assignee: SONOSIM, INC., Santa Monica, CA (US)

( * ) Notice: Subject to any disclaimer, the term of this patent is extended or adjusted under 35 U.S.C. 154(b) by 157 days.

(21) Appl. No.: 15/682,121

(22) Filed: Aug. 21, 2017

(65) Prior Publication Data

US 2017/0352294 A1    Dec. 7, 2017

Related U.S. Application Data

(63) Continuation-in-part of application No. 15/154,915, filed on May 13, 2016, now abandoned, which is a
(Continued)

(51) Int. Cl.
*G09B 23/28* (2006.01)
*G06F 3/041* (2006.01)
(Continued)

(52) U.S. Cl.
CPC ............ *G09B 23/286* (2013.01); *A61B 5/066* (2013.01); *A61B 8/4245* (2013.01);
(Continued)

(58) Field of Classification Search
CPC .......... G06F 3/03; G06F 3/033; G06F 3/0346; G06F 3/0354; G06F 3/03543; G06F 3/03545; G06F 3/03547; G06F 3/041; G06F 3/0414; G06F 2203/0383; G06F 2203/0384; G06F 2203/04104; G06F 2203/04105; A61B 5/0053; A61B 5/065; A61B 5/066; A61B 5/067; A61B 5/068; A61B 5/06; A61B 5/6843; A61B 8/00; A61B 8/42; A61B 8/4245; A61B 8/4254; A61B 8/4263; A61B 8/44; A61B 8/4444; A61B 8/4472; A61B 8/461; A61B 8/52; A61B 8/58;
(Continued)

(56) References Cited

U.S. PATENT DOCUMENTS 5,231,381 A    7/1993    Duwaer
5,609,485 A    3/1997    Bergman et al.
(Continued)

*Primary Examiner* — Keith L Crawley
(74) *Attorney, Agent, or Firm* — Cislo & Thomas, LLP

(57) ABSTRACT

A method for training an ultrasound user with a hand-held device having one or more first sensors to detect angular orientation of the device in one or more dimensions, and at least one two-dimensional surface device having one or more second sensors to detect translational position of the hand-held device in one or more directions, which communicates the angular orientation data from the hand-held device and the translational position data from the at least one surface device to a computer to display a virtual environment with a virtual hand-held device that moves in correlation with the hand-held device based on the angular orientation data from the hand-held device and the translational position data from the at least one surface device.

16 Claims, 12 Drawing Sheets

Related U.S. Application Data continuation-in-part of application No. 14/494,379, filed on Sep. 23, 2014, now abandoned.

(60) Provisional application No. 61/881,338, filed on Sep. 23, 2013.

(51) Int. Cl.
    *A61B 8/00*    (2006.01)
    *A61B 5/06*    (2006.01)
    *G06F 3/0346*  (2013.01)
    *A61B 5/00*    (2006.01)

(52) U.S. Cl.
    CPC .............. *A61B 8/4472* (2013.01); *A61B 8/58* (2013.01); *A61B 8/582* (2013.01); *G06F 3/0346* (2013.01); *G06F 3/0414* (2013.01); *A61B 5/6843* (2013.01)

(58) Field of Classification Search
    CPC .... A61B 8/582; G09B 23/281; G09B 23/285; G09B 23/286; G09B 23/30
    See application file for complete search history.

(56) References Cited

U.S. PATENT DOCUMENTS

| | | | |
|---|---|---|---|
| 5,678,565 A * | 10/1997 | Sarvazyan | A61B 1/0052 600/437 |
| 5,889,237 A | 3/1999 | Makinwa | |
| 6,122,538 A | 9/2000 | Sliwa et al. | |
| 2002/0076681 A1* | 6/2002 | Leight | G09B 23/28 434/273 |
| 2006/0020204 A1 | 1/2006 | Serra et al. | |
| 2008/0200807 A1 | 8/2008 | Wright et al. | |
| 2010/0179428 A1 | 7/2010 | Pedersen et al. | |
| 2010/0277422 A1 | 11/2010 | Muresianu et al. | |
| 2012/0238875 A1 | 9/2012 | Savitsky et al. | |
| 2013/0064036 A1 | 3/2013 | Lee et al. | |
| 2013/0158411 A1* | 6/2013 | Miyasaka | A61B 8/429 600/472 |
| 2014/0114194 A1* | 4/2014 | Kanayama | A61B 8/5215 600/459 |
| 2014/0272878 A1* | 9/2014 | Shim | G09B 23/30 434/272 |
| 2015/0056591 A1 | 2/2015 | Tepper et al. | |
| 2016/0328998 A1* | 11/2016 | Pedersen | G09B 23/28 |
| 2017/0046985 A1* | 2/2017 | Hendrickson | G09B 23/28 |

\* cited by examiner

METHOD FOR ULTRASOUND TRAINING WITH A PRESSURE SENSING ARRAY

CROSS-REFERENCES TO RELATED APPLICATIONS

This application is a continuation-in-part application of U.S. patent application Ser. No. 15/154,915, filed on May 13, 2016, which is a continuation-in-part application of U.S. patent application Ser. No. 14/494,379, filed on Sep. 23, 2014, which claims the benefit of U.S. Provisional Patent Application Ser. No. 61/881,338 filed Sep. 23, 2013, which applications are incorporated in their entirety herein by this reference.

BACKGROUND OF THE INVENTION

Field of the Invention

The present invention is directed to remote control systems in which two or more degrees of freedom of the remote device is controlled by remote control, and, in particular, systems in which both angular and translational movement of the remote device is remotely controlled by a remote control.

Description of the Related Art

Motion sensors that provide 3-DOF rotational control have become largely available in the consumer market and can be found in almost all smartphones and other portable computing devices. Their ubiquity is due in large part to modern advances in MEMS technology that allow manufactures to fabricate miniaturized Inertial Measurement Units (IMUs) at a low cost and at a large scale. Besides key advancements in industrial engineering, what makes rotational measurements units convenient to design and produce is that the Earth's gravitational and magnetic fields provide a readily available global fixed coordinate frame for the sensing components to use a reference. As a result, many devices that measure 3-DOF include electromechanical components that respond to gravity's acceleration (e.g., accelerometers) and the direction of Earth's magnetic pole (e.g., magnetometers).

Conversely, devices that can measure full 6-DOF (3 rotational and 3 translational) are substantially more difficult to produce, partly because there is no global reference frame for 3D positions that is easy to exploit. For large-scale measurements of position, one can use triangulation afforded by geostationary satellites in the form of global positioning systems, but the measurements provided by this modality are not reliable for small-scale applications where robustness and accuracy are important. Commercially available solutions that can measure 6-DOF accurately at a small-scale are generally expensive, difficult to set up (complex and large physical footprints), and suffer from several limitations (e.g., cumbersome calibration procedures) that make them impractical for general users. Common examples include multi-camera optical tracking systems (e.g., Polaris® Vicra®) and magnetic systems (e.g., Polhemus™ Patriot).

The problem can be largely simplified by further constraining the degrees of freedom of the sensing unit if doing so makes sense for the application at hand. For instance, knowing that the translational motion of the device is constrained to a flat plane or the surface of a sphere can simplify the computations needed to correlate raw measurements to the physical configuration of the device, and can improve accuracy. Furthermore, the designer may separate the sensing units that measure translation and rotation. This way, not only the complexity of the apparatus decreases, but it allows reusing commercially available devices at consumer prices that already measure each component separately without the need of designing and manufacturing custom hardware. The invention presented in this document hinges on the latter. Furthermore, while users can use gravity (the down vector) as a clear guidance to orient a sensing device that provides three rotational or angular DOFs to control a nearby remote system, a clear physical reference does not exist for translational motion. By using a tablet endowed with a display as a surface for translation, we can display a clear visual reference to the user to guide the motion.

The emergence of affordable, easy-to-use ultrasound simulators has spearheaded the development of novel low-cost motion tracking solutions. The challenge is to create sensors capable of measuring position and orientation as well as physical compression accurately and with minimal encumbrance for the user. Existing motion-tracking technologies and disclosed inventions used for tracking ultrasound probes for medical education and training (simulation) purposes are limited by the lack of realistic and affordable simulated compression. The inability to access reliable, portable, and affordable simulated ultrasound probe movement coupled with compression of tissues with resultant conversion of the compression forces into proportionate ultrasound data (image) deformation is a limitation to ultrasound simulation and training. This described invention introduces an effective solution that addresses multiple sensing requirements (i.e., motion tracking and compression) of ultrasound simulators. In one embodiment, the proposed solution consists of a single array of pressure sensors capable of measuring the contact mechanics of a probe or other relevant apparatus that is placed directly on its surface. From successive measurements of pressure distribution, a proposed tracking algorithm can extrapolate the exact position of the device as well as the amount of mechanical force exerted on the surface. This information is then coupled with ultrasound data with resultant proportionate tissue deformation. This approach overcomes a significant barrier to accurate and robust ultrasound simulation. In another embodiment we introduce the use of more traditional capacitive or resistive surfaces for tracking the position of a probe or other relevant apparatus.

Ultrasound simulators aim at reproducing the experience of using a real ultrasound transducer on a real patient as faithfully as possible. To achieve this goal, most commercially available products provide the user with a handheld device (scanning probe) that can sense its orientation and/or position in 3D space. The orientation and position of the scanning probe is then transmitted to a computer system that simulates how an ultrasound beam interacts with anatomy in the virtual environment and generates an appropriate ultrasound image on screen. In order to increase realism, the scanning probe is often designed to emulate the shape and weight of a real ultrasound transducer.

Many commercially available systems rely on 6 degree-of-freedom (DOF) magnetic, optical, or mechanical trackers. These tracking technologies are expensive, require a laborious set up, and suffer from several limitations. Magnetic trackers are highly susceptible to ferromagnetic interference and thus behave poorly in typical environments where the simulation station is surrounded by a variety of ferrous objects. Optical trackers are very accurate but require the user to maintain a clear line of sight between the handheld device and the tracking system, which is a major limitation in terms of usability. Mechanical trackers are bulky and unsuitable for many applications that require light and portable solutions. Furthermore, in most cases, the user needs to carefully install at least one component of the system externally to act as a reference adding to the system's complexity and encumbrance.

More recent simulators have achieved an adequate level of realism by restricting the sensing solution to 3DOF orientation and traded off the lack of position sensing with some other mechanism for identifying anatomical landmarks on the body. The success of these solutions is that they encapsulate the entirety of the motion sensing technology in the handheld scanning probe using modern MEMS ICs.

An alternative and very effective compromise is the pursuit of 5DOF solutions that restrict tracking of position to a 2D surface (not necessarily planar) and measure orientation in 3D. 5DOF tracking allows the system to measure the position of the handheld device as it slides over the profile of a body and registers its 3D orientation at each point. The advantage of this approach is that, with one fewer spatial dimension to track and a more constrained motion path, it enables engineers to build practical, accurate and self-contained solutions at lower cost compared to traditional solutions for full 6DOF tracking. Various authors have proposed 2D surface tracking solutions based on optical navigation sensors (used in computer mice) and optical tracking of non-repeating dot patterns. While acceptable, these optical solutions have several shortcomings: (1) They may not work well if the lens assembly of the optical sensor is not parallel to surface it tracks; and (2) the optics does not easily fit in objects whose contact surface is very small (e.g. the tip of a needle).

Hence, currently available and proposed simulated ultrasound probes do not have the required elements to accurately reproduce the movements and motions associated with real-life ultrasound guided procedures. This limits the ability to have simulation serve as a training and proficiency assessment tool.

In addition, in the context of ultrasound simulation, it is desirable to augment motion sensing with the ability to measure the mechanical pressure exerted by the scanning probe over a surface. In a real clinical setting, compressing the body of a patient by applying force with the ultrasound transducer during a scan causes the underlying soft tissue to deform, and ultrasound technicians use this phenomenon to differentiate various types of anatomical structures based on their elastic properties as observed in the ultrasound image.

SUMMARY OF THE INVENTION

One embodiment of the invention comprises a method for manipulating a remote device with a hand-held device having one or more first sensors to detect angular orientation of the device in one or more dimensions or planes, and at least one two-dimensional surface device having one or more second sensors to detect translational position (i.e. movement) of the hand-held device in one or more directions, which communicates the angular orientation data from the hand-held device and the translational position data from the at least one surface device to the remote device, and positions the remote device based on the angular orientation data from the hand-held device and the translational position data from the at least one surface device. Because the preferred embodiment implements the present invention as a training tool for ultrasound use, the hand-held device may be an ultrasound scanning probe.

In another embodiment, this described invention introduces an effective technology that addresses multiple sensing requirements (i.e., motion tracking and compression) of ultrasound simulators. Our invention accomplishes all these goals with very few components by using pressure sensing technology to measure position (2DOF) and compression simultaneously (1DOF). This technology, coupled with existing scanning probes capable of measuring orientation (3DOF), yields a solution that can measure 6 degrees-of-freedom (2 for position, 3 for orientation and 1 for compression). In order to differentiate our solution with traditional 6DOF (3 for position and 3 for orientation) motion trackers, we refer to this novel apparatus as a 5DOF+1 tracker. This approach overcomes a significant barrier to accurate and robust ultrasound simulation.

The present invention is an improvement over the prior art because (1) it can detect the position of any object of any shape and material as long as it rigid enough to exert an adequate amount of pressure on the sensing surface; (2) it can conform to most rigid curved surfaces; (3) it can tolerate a moderate amount of flex; (4) it can detect the position of multiple objects simultaneously; (5) it can measure physical force in addition to position without requiring an additional sensor; (6) it can function correctly underneath a moderately thick manikin skin; (7) it does not require direct line of sight, which is required by alternative optical tracking simulations; and (8) it provides a method to simulate ultrasound transducer or needle compression of tissues and provides objective data that can be extrapolated and applied to soft tissue deformation of ultrasound data.

DESCRIPTION OF THE PREFERRED EMBODIMENTS

Figure 1:
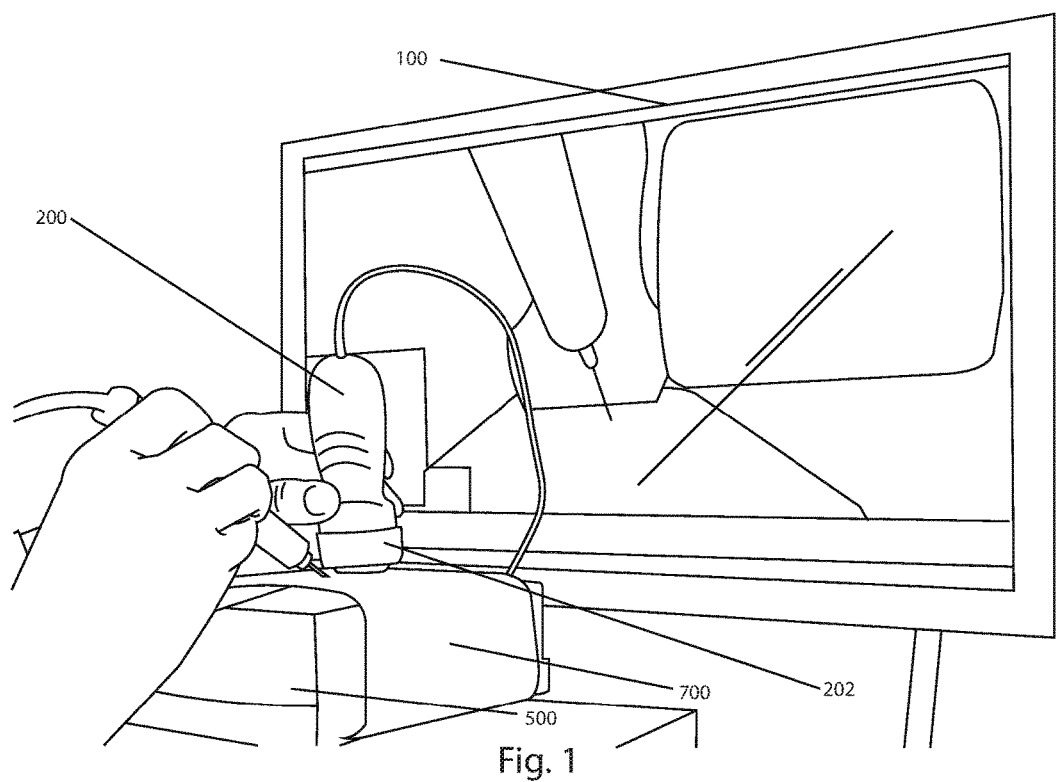
FIG. 1 shows an embodiment of the present invention in use.
Figure 2:
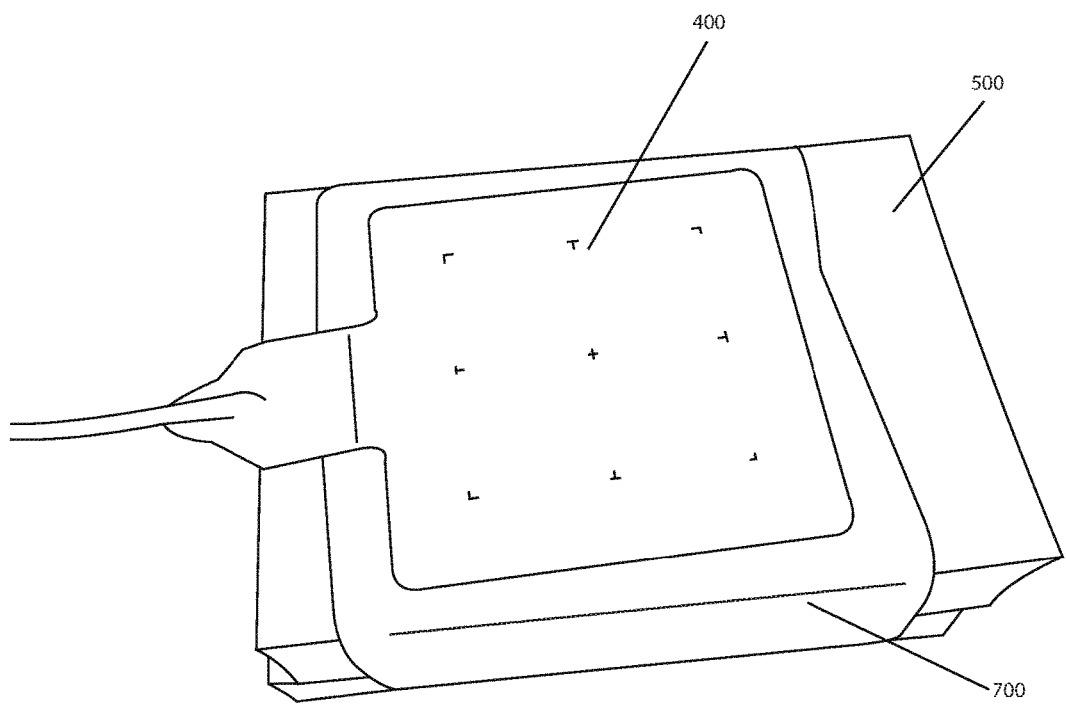
FIG. 2 shows a perspective view of the pressure sensing array on top of a skin simulator mounted on a flat scanning pad.

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

One embodiment of the invention presents a novel solution that allows a user to control a remote system in close proximity with three rotational or angular degrees-of-freedom (3-DOF), two translational degrees-of-freedom (2-D0F), and an optional compression component (1-DOF) for a total of six degrees-of-freedom (6-DOF). This device is useful for various applications where the user needs to control an object that is free to rotate around a movable pivot point, but the pivot point itself is constrained to move along a 2D surface. One notable application is the simulation of medical probes that must maintain constant contact with a patient's skin, such as ultrasound transducers.

Another embodiment utilizes a resistive or capacitive surface with an optional display such as on a computer, a tablet, a smartphone, and the like. The display if present serves as a visual reference to guide the user as it attempts to control the application on the remote system. For example, a tablet may display the image of a virtual mannequin and the remote system show the image of a two-dimensional (2D) ultrasound slice. This way as the user applies touch to a body part on the tablet's display, he or she will see a corresponding ultrasound image of the same body part on the remote system.

The apparatus comprises (1) a display device 100 with a touch-sensitive surface, an embedded display, and support for wired or wireless connectivity; (2) a handheld device or scanning probe 200 capable of measuring angular orientation that supports wired or wireless connectivity; (3) a remote computing system 300 that hosts the application software and can exchange data with both the tablet and the handheld controller; (4) an optional pressure sensitive tip 202 to measures the amount of mechanical pressure exerted (compression).

If a capacitive touch sensing surface is chosen, the handheld device or probe 200 preferably has a rubbery tip 202 that can be detected by the touch sensitive surface and slides comfortably on it. The user places the display 100, such as a tablet, on a stable support such as a table or his own lap and slides the handheld device 200 on the surface of the tablet. By doing so, the motion controller relays three rotational DOFs in the traditional two orthogonally spaced dimensions or planes, while the tablet relays the remaining two translational DOF in the traditional two orthogonally spaced directions to the remote system. If a pressure sensitive tip 202 is available as part of the handheld device 200, the system 300 provides an additional one-DOF for compression. This apparatus provides a simple and inexpensive way for consumers to control a remote system with 6-DOF. Additionally, the tablet will display a reference for transla-tional motion, thus offering a distinct advantage over alternative solutions for 5-DOF or 6-DOF sensing that do not provide any clear and adaptable reference to the user.

In the preferred embodiment, the problem of measuring the translational position and angular orientation of a device in 3D space is reduced from 6-DOF to 5-DOF by constraining the motion to a 2D surface, while retaining 3-DOF for rotations. The two translational components of the motion are measured by exploiting the touch surface of a tablet device such as the Apple iPad or other popular Android™ devices. The rotational or angular components of the motion are measured by a low-cost handheld 3-DOF motion controller. Such devices are widely available and they generally operate by fusing measurements provided by various Inertial Measurements Units (IMUs) and other sensors, although they may rely on different operating principles, such as electromagnetic, optical, or mechanical positioning. However, the advantage of inertial sensors is that they do not require an external reference component to operate and they are preferable for compact and portable solutions.

By covering the tip of the handheld device 200 with a soft flexible tip 202 with the appropriate material properties, the 3-DOF sensor can be simultaneously used as stylus to trace a path on the touch surface. Alternatively touch surfaces exist that do not require a special tip for sensing, such as 4-wire or 5-wire resistive displays similar to the one used in the popular Nintendo® DS and other low-cost touch sensitive devices. Alternatively, a regular stylus may be attached or incorporated with the handheld motion controller directly. A stylus has a narrow tip that may provide better feedback as to where the contact point between the controller and the touch surface is. Additionally, there are commercially available active styli that can relay richer positional information to the host tablet. Examples are the Wacom® Intuous® Creative Stylus for iOS or other styli designed specifically for certain Android™ devices, such as the Samsung® Galaxy Note®. In particular, the Wacom® Intuous® Creative Stylus has a pressure sensitive tip and can relay 2048 levels of compression through the host tablet via Bluetooth®.

This invention allows a user to relay full 6-DOFs to a remote device with one smooth hand motion. Of course, each sensor needs to independently or cooperatively (separate sensors relay to the tablet and the tablet relays to the remote system) send its measurements to the remote host that runs the application software to be controlled by the apparatus. Many solutions are possible depending on the type of tablet and handheld controller used. For instance, the tablet may send touch positions via wi-fi and the handheld controller via Bluetooth®.

This invention finds a natural application as a controller for medical simulations of ultrasound imaging, such as the SonoSim® Ultrasound Training Solution. The remote system in the present invention can be any computer running the software, such as a laptop, desktop, tablet, smart phone, personal digital assistant, any other mobile device, and the like. The remote system shows:
  a. A 3D rendering of virtual body from the outside;
  b. A 3D rendering of an ultrasound probe placed on the region of the body that the user wishes to study;
  c. An overlay showing a reconstructed or simulated ultrasound image that matches the region of the body being swept by the rendered ultrasound probe; and
  d. A UI that allows the user to interact with the application.

The handheld device 200 combined with the tablet touch surface lets the user define the position and orientation of the virtual probe on the surface of the body in the software by altering its orientation and position within the tablet surface. Additionally, if pressure sensitivity is available it can be used to control the amount of compression applied against the virtual body, which in turn will cause soft tissues to deform in the simulation.

The invention presented in this document, allows the user to orient the virtual probe by means of the handheld 3-DOF rotational controller and to slide the probe along the surface of the body by translating and/or axially compressing the handheld controller on the surface of the tablet. Moreover, the tablet communicates with the remote system to establish which image to display when the user interacts with it. Preferably the tablet will display a top view of the part of the body that the user has selected. Since the physical extent of the tablet is known a priori, the tablet software can be designed so that the range of motion afforded by the user corresponds exactly to the extent on the body that he or she wishes to study.

In another embodiment, the invention comprises: (1) a Pressure Sensing Array 400 (PSA) packaged with electronics; (2) a computer system 300 to run the ultrasound simulator, process sensor data, and communicate with the pressure sensing array 400; (3) a scanning probe 200 with an embedded sensor for measuring orientation and able of communicating with the computer 300; and (4) a semi-rigid scanning surface or a scanning pad 500.

User Experience (1) The user places the PSA 400 on a semi-rigid surface;

(2) The user places the scanning probe 200 over the PSA 400;

(3) The PSA 400 relays a measurement of the pressure distribution to the computer system 300;

(4) The scanning probe 200 relays a measurement of orientation to the computer 300;

(5) The computer system 300 processes the measurements of pressure distribution and orientation, and estimates the position of the scanning probe 200 on the PSA 400 using the proposed algorithm;

(6) The estimated position (i.e. translational movement) and orientation (i.e. angular movement) of the scanning probe 200 is used in the ultrasound simulator to place the virtual probe and the scanning plane correctly within the virtual scene on a virtual body, such as a virtual patient;

(7) The simulator uses this information to compute an ultrasound image corresponding to the estimated position and orientation of the scanning plane;

(8) The user exerts some force on the scanning probe 200 to apply additional pressure on the PSA 400;

(9) The PSA 400 relays the measurement of pressure distribution to the remote computer system 300; and

(10) The computer 300 measures the change in pressure distribution and updates the simulation to show soft tissues deforming in the ultrasound image.

As the user slides the scanning probe 200 over the PSA 400 and varies the amount of physical force applied on the PSA 400 by the scanning probe 200, compression data is generated and transmitted to the computer system 300. The compression data reflects the pressure distribution caused by the scanning probe 200 on the PSA 400. The computer 300 uses successive measurements of pressure distribution to track the translational movement (i.e. position) of the probe 200 and the state of compression in the virtual environment, mimicking the sequence of actions that the user performs on the PSA 400.

Pressure Sensing Array

There are two general operating principles that are used to manufacture adequately accurate pressure sensors suitable for the present application: Resistive and Capacitive.

Resistive Pressure Sensors

A resistive pressure sensor is any physical assembly that produces changes in resistance in response to an applied physical force. These sensors rely on the fact that the resistance of a conductive element is a function of its geometry; thus, modifying the geometry of the sensing element causes a measurable change in resistance under load.

Many implementations of this operating principle exist commercially and are known to those skilled in the art. Of particular interest are resistive sensors that can measure both the 2D position and the weight of the pressure point. Many brands of off-the-shelf resistive 4-wire or 5-wire touch screens are adequate for this purpose.

The main limitation of standard touch screens is that they can only detect a single point of contact at a time. However, various vendors have introduced resistive solutions to the market that can combine multiple individual resistive force cells to provide a full measurement of pressure distribution and multiple simultaneous contact points.

Capacitive Pressure Sensors

Capacitive pressure sensors are composed of two conductive layers separated by thin deformable dielectric. This assembly creates a capacitor with a known value of capacitance at rest. A load placed on the device, causes the distance between the conductive layers to vary causing a measurable change in capacitance. An electronic circuit then measures the change in capacitance and relays the value to a processor, which in turn computes an estimate of the force applied on the sensor. Combining a multitude of such capacitive elements in a tightly packed array with an appropriate flexible interconnect, produces a sensor assembly capable of measuring pressure distributions very accurately. Such devices are commercially available and known to those skilled in the art.

Others

While Resistive and Capacitive sensor are the most common low-cost solutions for measuring pressure distribution, there are many other operating principles that can be exploited to build a device equivalent in function. For instance, laser interferometry can be used to correlate small deformations on a surface to a distribution of pressure applied to it.

Any device capable of measuring the distribution of pressure applied to its surface fulfils the intent of this invention.

Algorithm

The system proposed in this invention relies on an algorithm that translates readings of pressure distributions into estimates of position. We describe a representative algorithm that constitutes a preferred embodiment of the invention, but practitioners skilled in the art can envision multiple equivalent algorithms that are similar in spirit to the one proposed and accomplish the same goal. We emphasize that the key innovation introduced by this invention is the concept of using a pressure sensing array to measure the position of an object on its surface and not necessarily the details of the algorithm presented in this section.

In the following we describe the preferred algorithm by considering progressively more difficult scenarios.

Single Pressure Distribution and Fixed Orientation

Figure 8:
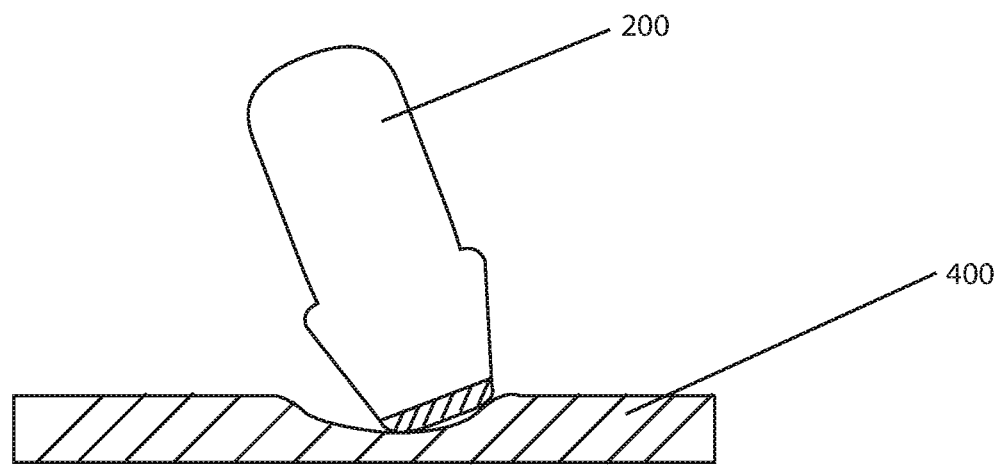
FIG. 8 a scanning probe deforming the pressure sensing array and a corresponding surface plot of the pressure distribution due to the pressure applied to the pressure sensing array.
Figure 8:
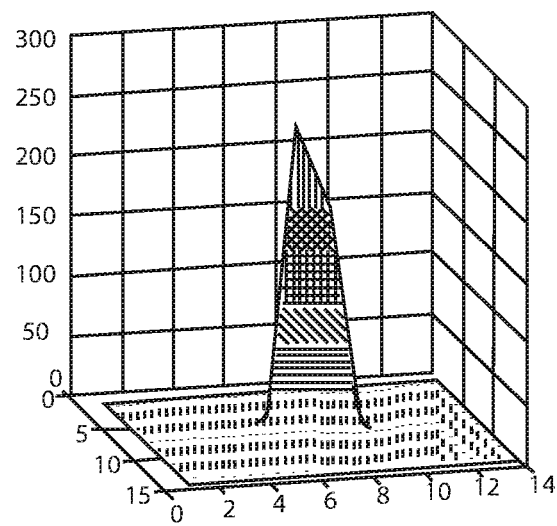

We start by considering the simplified case in which we assume that there is a single object in contact with the PSA (FIG. 8). We also assume that the orientation of the object does not change over time, so that the profile of the pressure distribution (pressure distribution plot) always looks the same as the object is translated over the PSA, regardless of object's geometry. In this case, the algorithm consists merely of computing the center of pressure of the pressure distribution and using that estimate as the position of the object. On a pressure distribution plot, the center of pressure may be determined by the peak location on the pressure distribution plot.

Multiple Distinct Pressure Distributions and Fixed Orientation

Figure 9:
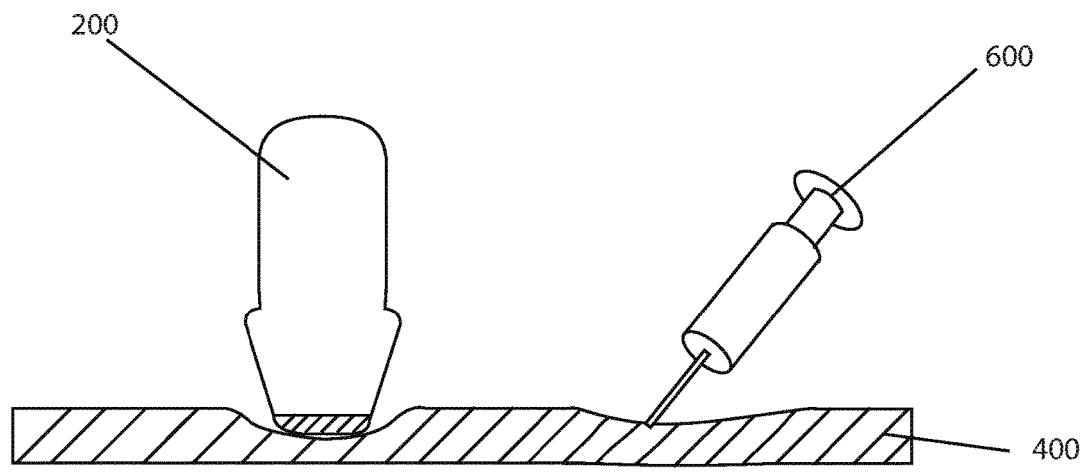
FIG. 9 shows a scanning probe and a needle controller deforming the pressure sensing array and a corresponding surface plot of the pressure distribution due to the pressure applied by the scanning probe and the needle controller.
Figure 9:
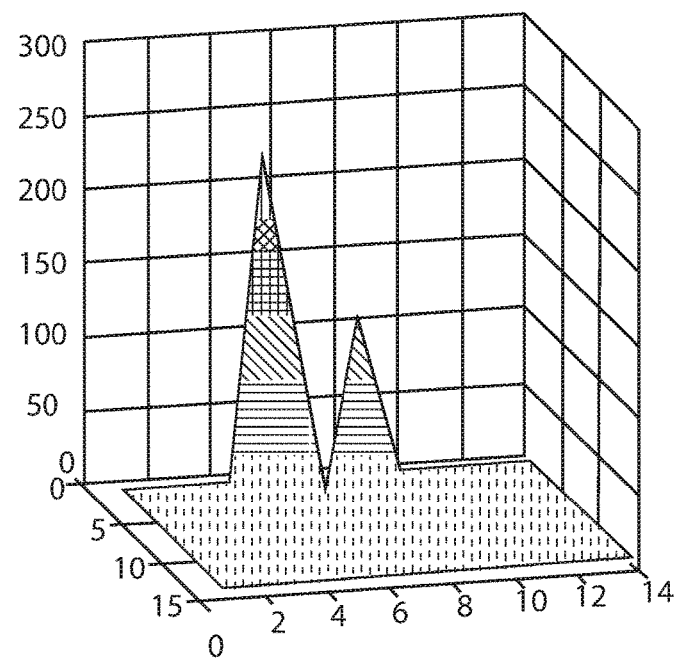

We now consider the case where multiple objects are placed on the surface, thus producing multiple contact points (FIG. 9). We also assume for simplicity that the pressure distributions of each object are not overlapping. Let I be the measured pressure distribution represented as a grayscale image. The algorithm proceeds as follows:

Apply a threshold filter on the image to isolate areas where the measured pressure exceeds a predetermined value. This step produces a binary image T(I).

(1) Isolate individual contiguous contours on the image to obtain a set of contours $C(T(I))=[C1, C2, \ldots, Cn]$; and (2) Compute the center of pressure of each contour Ci and use it as estimate of the position of each object.

Single Pressure Distribution and Variable Orientation

Figure 11:
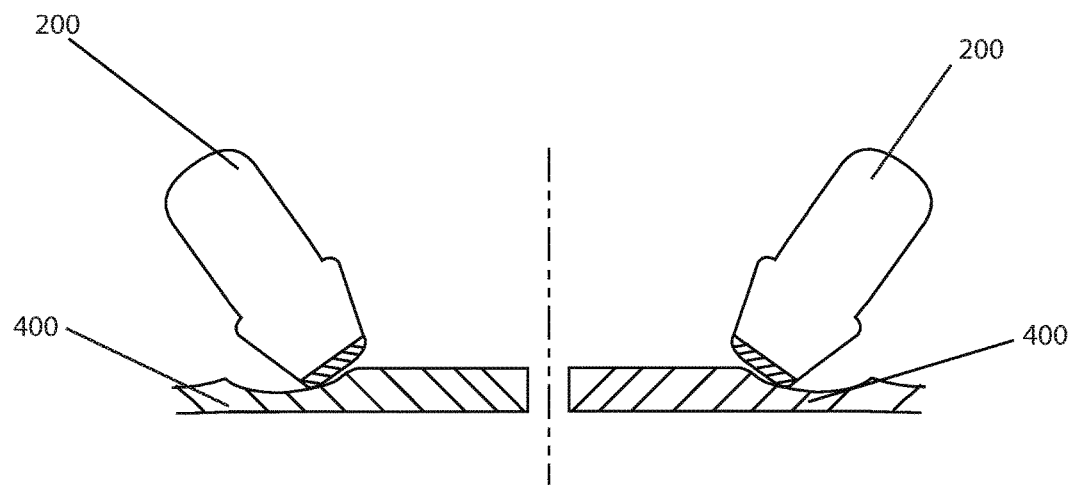
FIG. 11 shows a scanning probe moving from one direction to another direction and corresponding surface plots of the change in the pressure distribution due to the movement.
Figure 11:
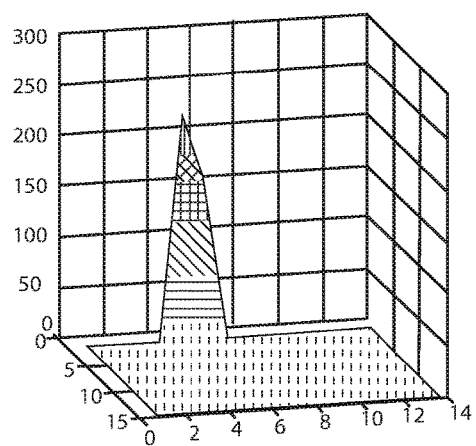
Figure 11:
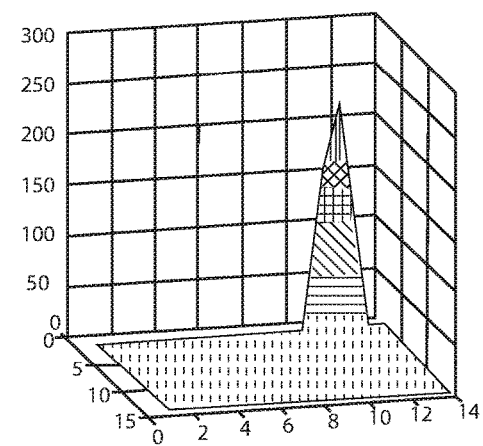
Figure 12:
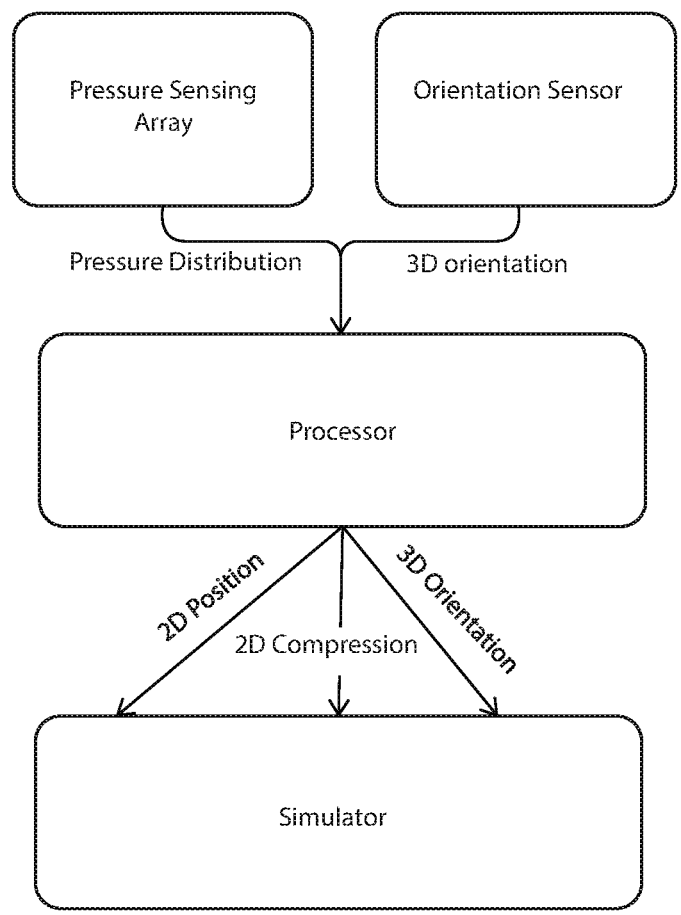
FIG. 12 shows a high-level flow diagram of the process of an embodiment of the present invention.

When the orientation of an object in contact with the PSA varies, so does the profile of its pressure distribution (except for the simplest geometries). In other words, when there is an orientation variation in the scanning probe 200, the pressure distribution plot shows a different profile as demonstrated in FIG. 11. FIG. 11 shows two different orientations of the scanning probe 200 and their respective pressure distribution plots below them to show the different distribution plot profiles based on the orientation of the probe 200. This phenomenon can cause a naive algorithm to misinterpret even slight changes of orientation as large changes in position. To address this problem, we first chose the projection of the object's center of gravity onto the scanning surface as the true position of the object that we seek to measure.

If there is a way to independently measure the orientation of the object (which we assume it is true for the preferred embodiment) and the geometry of the object is known a priori, we can use the provided information to compute an offset between the center of pressure (measured position) and the projection of the object's center of gravity onto the scanning surface (true position) to compensate for the changing orientation of the scanning probe 200. We precompute the offsets by populating a look-up table (or database) that maps discrete values of orientation to corresponding values of offset. In special cases, when the geometry profile of the contact surface is simple enough, the mapping between orientation and offsets can be computed in closed form without requiring a look-up table. Therefore, when the offset matches one of the values in the look-up table (or database), then the system knows that the orientation of the scanning probe 200 has changed rather than having undergone a translational movement. As such, calculation of the offset allows the system to differentiate between changes in angular orientation versus translational movement of the scanning probe 200.

Multiple Overlapping Pressure Distributions and Fixed Orientation

Figure 10:
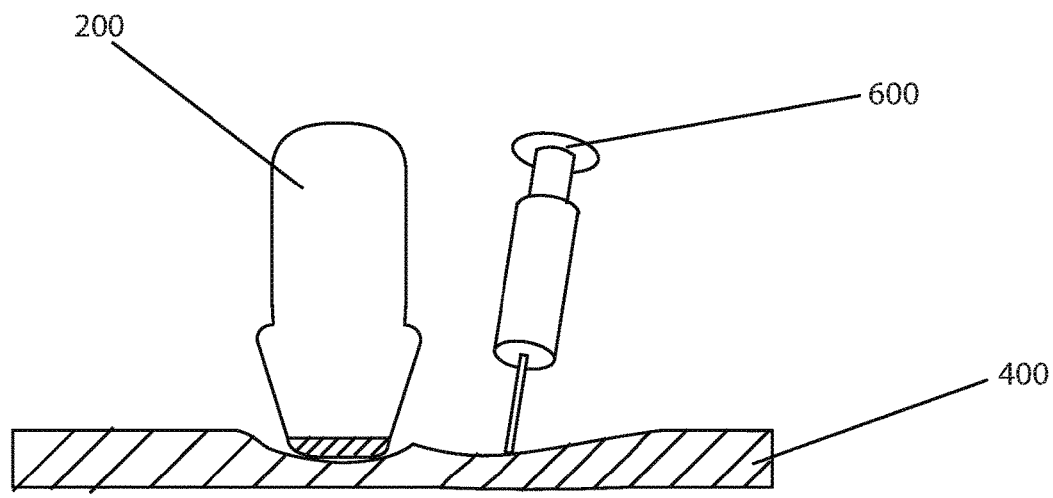
FIG. 10 shows a scanning probe and a needle controller deforming the pressure sensing array and a corresponding surface plot of the pressure distribution due to the pressure applied by the scanning probe and the needle controller.
Figure 10:
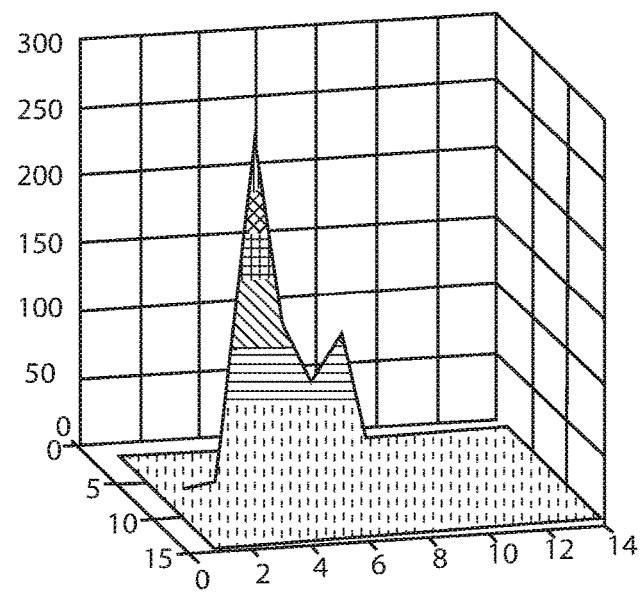

When the objects in contact with the surface are very close to each other, the corresponding pressure distributions will overlap and the trivial algorithm cannot cleanly disambiguate the position of each object (FIG. 10). We still assume that the shape of each object is distinct enough that its pressure signature can be used to uniquely identify the object. In this case the algorithm will need to first run a classifier to distinguish the pixels on the image that correspond to each object and then compute the center of pressure of each contiguous region of pixels in the same class. This form of classification is well-known to practitioners and depending on the complexity configuration can vary from simple signal processing filters to complex applications of machine learning. By calculating the centers of pressure for the second device and the scanning probe, the translational movement of each can be distinguished.

Multiple Overlapping Pressure Distributions and Variable Orientation

This is the case that is most interesting for real-life applications. One skilled in the art can derive the final algorithm by combining the components of the algorithm described above in light of the teachings in this application. Namely:

Use a classifier to identify the pressure distribution of each distinct object;

Compute the center of pressure of each contiguous set of pixels in the same class;

For each class compute an offset from the center of pressure based on the measured orientation of the object; and Use the location of the center of pressure offset by the computed amount as an estimate of position for each object.

Measuring Compression

By the nature of using a pressure sensing device to track the position of one or more objects, it should be apparent to those skilled in the art that the amount of physical compression applied on the surface can be readily computed by calculating the force applied on the center of pressure. Furthermore, most ultrasound simulators do not need an exact measurement of force and can produce adequate visual results with only approximate relative measurements of the applied force. Therefore, the skilled practitioner can build the desired functionality without needing to accurately calibrate the PSA, which further reduces cost and complexity. In other words, for this invention it suffices to have a device that can measure the distribution of pressure in some arbitrary units that do not need to correspond to well-defined physical units.

Tracking and Filtering

As with any practical sensor technology, the estimated position may be affected by noise and other confounding factors that can degrade the quality of the output. Traditional and well-understood algorithms for tracking and data filtering, such as Kalman filters, can be used without modification for this application. We note that tracking objects from a sequence of pressure distributions is equivalent in many ways to well-understood problem of tracking objects in a sequence of video frames.

Needle-Guided Procedures

One of the distinct advantages of the present invention is that it allows practitioners to build a sensing component that can simultaneously detect the 2D position, orientation, and applied force of multiple objects simultaneously, such as the scanning probe 200 and a secondary device, such as a needle or syringe. In the context of ultrasound simulation, this solution is highly advantageous as it allows the user to practice needle procedures with ultrasound guidance in a simulated environment. In order to do so, the set-up comprises:

(1) A scanning probe 200 that can relay measurements of its orientation to a computer system 300;

(2) A needle controller 600, a device modelled after a syringe that can relay measurements of its orientation to the computer system 300;

(3) A PSA 400; and (4) the computer system 300 running the simulator to display a virtual probe and a virtual secondary device in a virtual environment with a virtual body.

Using the principles described earlier, the computer system 300 can estimate both the position and orientation of the scanning probe 200 and scanning needle 600 simultaneously and guide the user through the sequence of steps that clinicians must be comfortable with when performing procedures under ultrasound guidance. The ability to classify each object in the snapshots of pressure profile is greatly simplified by the fact that the pressure signature of the scanning probe and the needle tip are widely distinct.

Conformability

As demonstrated by several commercially available products, Pressure Sensing Arrays (PSAs) can be built with flexible electronics and tolerate a moderate amounts of flex. This property makes them ideal for practical simulators, phantoms, and medical manikins allowing practitioners to place them on semi-rigid curved surfaces that are representative of body shapes.

Embodiments

In this section we present a collection of useful embodiments of the present invention with the purpose of highlighting the usefulness and relevance of the invention to advance the state-of-the-art in ultrasound simulation. In no way, is this selection intended to be exhaustive.

Scanning Pad with PSA Placed Externally

The scanning pad 500 may be a semi-rigid surface that may be planar or curved on the exterior (FIGS. 1-5). The scanning pad is essentially a physical surface that hosts the PSA 400 and mimics the type of curves and contours on the human body. The user can place it on a table on his/her lap, or any other stable surface to interact with an ultrasound simulator running on an external computer system. In the simplest case, the PSA 400 can be placed on top of the scanning pad 500 and appropriately connected to the computer 300 running the simulator by either a wired or wireless connection.

Scanning Pad with PSA Placed Underneath a Soft Skin Medium

Figure 3:
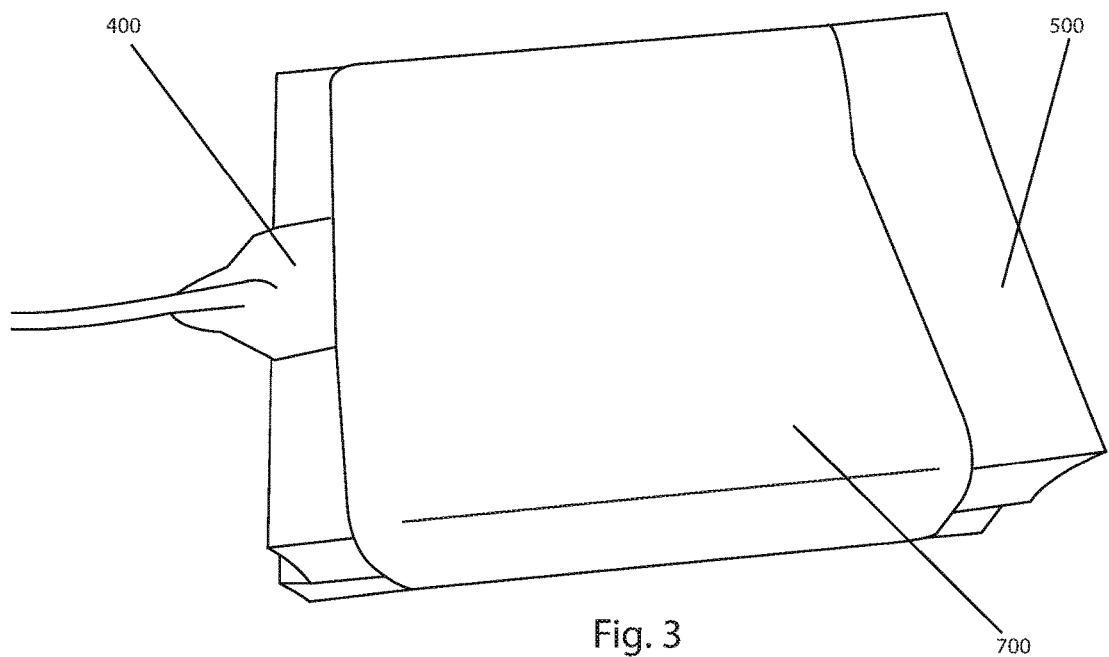
FIG. 3 shows a perspective view of the pressure sensing array mounted on a flat scanning pad but underneath the skin simulator.
Figure 4:
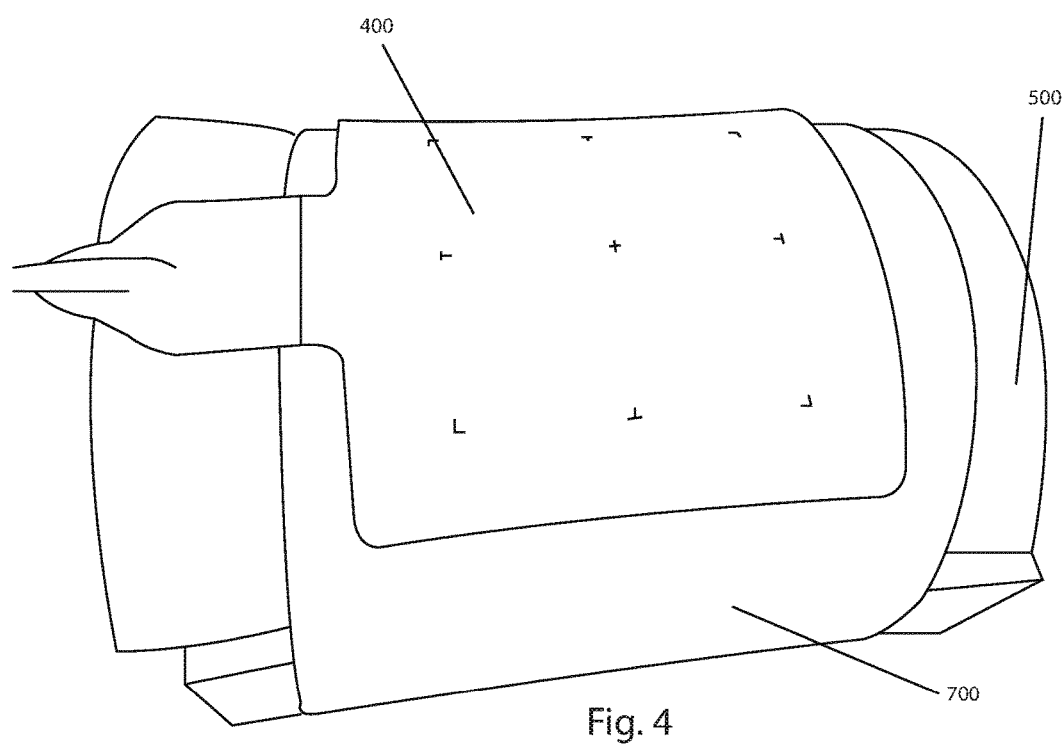
FIG. 4 shows a perspective view of the pressure sensing array on top of a skin simulator mounted on a curved scanning pad.
Figure 5:
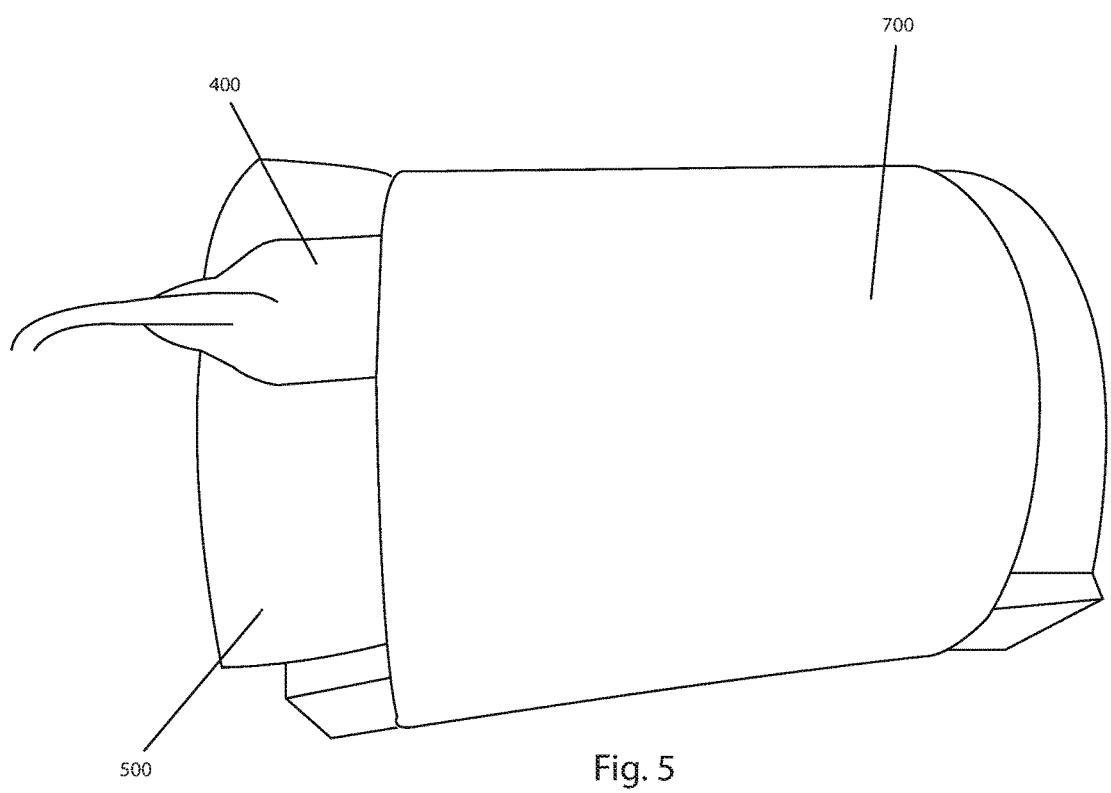
FIG. 5 shows a perspective view of the pressure sensing array mounted on a curved scanning pad underneath a skin simulator.

This embodiment is analogous to the one described in the previous section, but it places the PSA 400 underneath a soft skin simulator 700 made of a soft deformable material, such as foam (FIG. 3). The skin simulator 700 is a surface layer that possesses mechanical properties, characteristics, and appearance similar to skin. Any material that can deform and transmit the force applied on its surface to the PSA 400 is acceptable for this application. The PSA 400 can be positioned underneath the skin simulator 700 peiiiianently or provide an easily accessible pocket that allows the user to insert and subsequently remove the PSA 400 as needed.

One technical advantage of placing the PSA 400 underneath a skin simulator 700 is that the skin simulator 700 can help distribute the pressure distribution of an object and therefore acts as a mechanical low-pass filter that can reduce noise and simplify the detection of position. The thickness and material properties of the skin control the amount of filtering and allow engineers to tune the response of the system to their needs.

Medical Manikin with Single or Multiple PSAs Placed Externally

Figure 6:
FIG. 6 shows a perspective view of the pressure sensing array mounted on a mannequin.

By placing the PSA 400 on a medical manikin 800, engineers can expand the capabilities of traditional medical simulations by providing a low-cost and accurate way to measure translation, orientation, and applied force of both a scanning probe 200 and needle controller 600 over a medical manikin 800. Placing the PSA 400 externally is the simplest configuration and can be easily used to retrofit existing manikins (FIG. 6). Practitioners may choose to place a single PSA 400 or multiple connected PSAs 400 to extend the physical scanning area available to the user.

Medical Manikin with Single or Multiple PSAs Placed Underneath a Soft Skin

Figure 7:
FIG. 7 shows a perspective view of the pressure sensing array mounted on a mannequin underneath the skin simulator.

This configuration is analogous to the one described in the previous section, but it places the single PSA 400 or multiple PSAs 400 underneath a soft deformable skin similar 700 (FIG. 7). This embodiment is useful for more permanent installations, is more discreet, and enjoys the same advantages of described in the section describing the scanning pad 500.

Extensions

One potential challenge of the proposed invention is that the user may inadvertently apply pressure on the PSA 400 with his/her wrist or other items not meant to be tracked by the system. Even though a robust classifier described in the technical literature may detect such outliers, we devise in this invention a hardware solution that can greatly increase robustness. The idea is to cover the PSA 400 with two additional layers:

(1) A strong insulator; and (2) A conductive sheet.

The conductive sheet is connected to a microcontroller endowed with the proper hardware and firmware capabilities to measure capacitance. This apparatus allows the microcontroller to detect contact with skin using well-known techniques employed in the implementation of capacitive touch sensing solutions. When the microcontroller detects contact with skin, it reports this event to the computer unit, which in turn can turn off position sensing to prevent registering an outlier position.

If instead of a single conductive sheet, the implementer integrates a full touch sensing array, such as the projected capacitive components used in smartphones and tablets, the software can detect the exact region of contact between the skin and the surface of the PSA. Then the algorithm for estimating positions from the pressure sensing distribution can filter out this region of contact known to be caused by the spurious touch.

While the present invention has been described with regards to particular embodiments, it is recognized that additional variations of the present invention may be devised without departing from the inventive concept.

What is claimed is:

1. A method for ultrasound training, comprising:

a. providing a scanning probe having sensors to collect angular orientation data of the scanning probe in three dimensions;

b. providing a pressure sensing array having sensors to collect compression data on the pressure sensing array applied by the scanning probe;

c. providing a scanning pad upon which the pressure sensing array is mounted; and d. providing a skin simulator to place on top of the pressure sensing array to mimic a human subject, e. wherein the angular orientation data from the scanning probe and the compression data from the pressure sensing array are transmitted to a computer, f. wherein the computer is configured to calculate translational position of the scanning probe on the pressure sensing array based on the compression data, wherein the compression data is used to generate a pressure distribution plot identifying a center of pressure of a force applied by the scanning probe on the pressure sensing array, wherein the center of pressure is used to determine the translational position of the scanning probe, g. wherein the computer is configured to calculate angular orientation of the scanning probe based on the angular orientation data, h. wherein the computer is configured to calculate an offset between the center of pressure and a center of gravity of the scanning probe to differentiate between changes in angular orientation and translational movement of the scanning probe, and i. wherein the computer is configured to create a virtual environment displaying a virtual scanning probe and a virtual body, wherein movement of the virtual scanning probe along the virtual body correlates with movement of the scanning probe along the pressure sensing array.

2. A method for ultrasound training, comprising:
a. providing a scanning probe having sensors to collect angular orientation data of the scanning probe in three dimensions; and
b. providing a pressure sensing array having sensors to collect compression data on the pressure sensing array applied by the scanning probe,
c. wherein the angular orientation data from the scanning probe and the compression data from the pressure sensing array are transmitted to a computer,
d. wherein the computer is configured to calculate a translational position of the scanning probe on the pressure sensing array based on the compression data,
e. wherein the computer is configured to calculate an angular orientation of the scanning probe based on the angular orientation data, and
f. wherein the computer is configured to create a virtual environment displaying a virtual scanning probe and a virtual body, wherein movement of the virtual scanning probe along the virtual body correlates with movement of the scanning probe along the pressure sensing array,
g. wherein the compression data is used to generate a pressure distribution plot identifying a center of pressure of the scanning probe on the pressure sensing array, wherein the center of pressure is used to determine the translational position of the scanning probe, and
h. the method further comprising determining an offset between the center of pressure and a center of gravity of the scanning probe to differentiate between changes in the angular orientation and the translational position of the scanning probe.

3. The method of claim 2, further comprising placing the pressure sensing array on a scanning pad.

4. The method of claim 3, further comprising placing a skin simulator on the pressure sensing array to mimic a human subject.

5. The method of claim 4, wherein the scanning pad is a manikin.

6. The method of claim 2, further comprising providing a secondary device to transmit angular orientation data of the secondary device to the computer to display a virtual secondary device in the virtual environment.

7. The method of claim 6, further comprising determining a first center of pressure for the scanning probe and a second center of pressure for the secondary device to distinguish a translational position of the secondary device from the translation position of the scanning probe.

8. The method of claim 2, wherein the computer is configured to display a pressure distribution plot on the display with the virtual scanning probe and the virtual body, wherein the pressure distribution plot is generated based on the compression data.

9. The method of claim 2, wherein the pressure sensing array calculates an average force applied by the scanning probe to collect the compression data for calculating physical pressure applied on the pressure sensing array.

10. A method for ultrasound training, comprising:
a. using a scanning probe having sensors to detect an angular orientation of the scanning probe in one or more dimensions;
b. placing the scanning probe over a pressure sensing array to detect a translational position of the scanning probe in one or more directions based on a pressure distribution created by the scanning probe exerting pressure on the pressure sensing array; and
c. viewing a display device displaying a virtual probe in a virtual environment created by a computer, wherein the virtual probe performs movement based on the angular orientation from the scanning probe and the translational position from the pressure sensing array to correlate with movement of the scanning probe along the pressure sensing array,
d. wherein compression data generated by force applied by the scanning probe on the pressure sensing array is used to generate a pressure distribution plot identifying a center of pressure of the scanning probe, wherein the center of pressure is used to determine the translational position of the scanning probe, and
e. wherein an offset is calculated between the center of pressure and a center of gravity of the scanning probe to differentiate between changes in angular orientation and translational position of the scanning probe.

11. The method of claim 10, further comprising placing the pressure sensing array on a scanning pad.

12. The method of claim 11, further comprising placing a skin simulator on the pressure sensing array to mimic a human subject.

13. The method of claim 10, further comprising using a secondary device to transmit angular orientation data of the secondary device to the computer to display a virtual secondary device in the virtual environment.

14. The method of claim 13, wherein centers of pressure for the secondary device and the scanning probe are calculated to distinguish a translational position of the secondary device from the translational position of the scanning probe.

15. The method of claim 10, wherein the computer is configured to display a pressure distribution plot on the display device with the virtual scanning probe, wherein the pressure distribution plot is generated based on the compression data.

16. The method of claim 10, wherein the pressure sensing array calculates an average force applied by the scanning probe to collect the compression data for calculating physical pressure applied on the pressure sensing array.

* * * * *